(12) United States Patent
Weindel et al.

(10) Patent No.: US 6,197,594 B1
(45) Date of Patent: *Mar. 6, 2001

(54) WHITE TRIGGER PREPARATIONS FOR IMPROVING THE SIGNAL DETECTION IN BIOLUMINESCENT AND CHEMILUMINESCENT REACTIONS

(75) Inventors: Kurt Weindel; Hans Hornauer, both of Habach (DE)

(73) Assignee: Roche Diagnostics GmbH, Mannheim (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/552,795

(22) Filed: Nov. 3, 1995

(30) Foreign Application Priority Data

Nov. 4, 1994 (DE) .................................................. 44 39 348

(51) Int. Cl.[7] .......................... G01N 21/76; G01N 33/53; G01N 33/58
(52) U.S. Cl. .......................... 436/172; 422/82.05; 422/52; 435/7.1; 435/7.9; 436/537; 436/800; 436/805; 436/807
(58) Field of Search .................. 435/7.92–7.95, 435/7.1, 7.9; 436/172, 525–532, 537, 56, 63, 800, 805, 807, 518; 422/82.05, 52

(56) References Cited

U.S. PATENT DOCUMENTS

| 4,097,338 | 6/1978 | Konttinen et al. . |
|---|---|---|
| 4,540,660 | 9/1985 | Harte et al. . |
| 4,622,294 | * 11/1986 | Kung et al. . |
| 4,640,898 | * 2/1987 | Halfman . |
| 4,745,074 | * 5/1988 | Schreir et al. . |
| 4,778,763 | * 10/1988 | Makiguchi . |
| 5,017,009 | 5/1991 | Schutt et al. . |
| 5,082,628 | * 1/1992 | Andreotti . |
| 5,128,241 | * 7/1992 | Imai et al. . |
| 5,296,355 | * 3/1994 | Shutoh et al. . |

FOREIGN PATENT DOCUMENTS 2076709 2/1994 (CA) .

OTHER PUBLICATIONS

International Publication No. WO 90/06503 published Jun. 14, 1990.
Websters II New Riverside University Dictionary, Houghton Mifflin Company (1994) p. 708 USA.*

* cited by examiner

Primary Examiner—Anthony C. Caputa
Assistant Examiner—Stephen Gucker
(74) Attorney, Agent, or Firm—Nikaido Marmelstein Murray & Oram, LLP

(57) ABSTRACT

The present invention concerns a method for the detection of an analyte in a sample liquid by luminescence measurement according to the principle of a ligand-receptor assay, e.g. an immunoassay or a hybridization assay or a combination thereof, wherein a sample liquid is incubated with at least one receptor which carries a luminescent label and the presence or/and the amount of the analyte to be detected is determined in the sample liquid by measuring the luminescence in a measuring medium containing dispersed components.

24 Claims, No Drawings

WHITE TRIGGER PREPARATIONS FOR IMPROVING THE SIGNAL DETECTION IN BIOLUMINESCENT AND CHEMILUMINESCENT REACTIONS

DESCRIPTION

The present invention concerns a method for the detection of an analyte in a sample liquid by a luminescence measurement according to the principle of a ligand receptor assay, e.g. an immunoassay or a hybridization assay or a combination thereof, wherein a sample liquid is incubated with at least one receptor which carries a luminescent label and the presence or/and the amount of the analyte to be detected is determined in the sample liquid by luminescence measurement.

The use of luminescent direct labels such as e.g. isoluminol or acridinium compounds or enzyme-amplified luminescent labels such as e.g. horseradish peroxidase/luminol or alkaline phosphatase/stabilized dioxetans as a detection system in immunological test procedures has the advantage over other test systems such as radioactive marker groups of a higher sensitivity (see among others McCapra F. and Beheshti I. in Knox van Dyke (publ.): Bioluminescence and Chemiluminescence; Instruments and Applications, Vol. 1, 9–42 1985; Barnard G. J. R. et al. in Knox van Dyke (publ.): Bioluminescence and Chemiluminescence; Instruments and Applications, Vol. 1, 151–183, 1985; Weeks I. et al. in de Luca M. A. and McElroy W. D. (publ.): Methods in Enzymology, Vol. 133, 366–387, 1986; McCapra F., et al., Journal of Bioluminescence and Chemiluminescence 4, 51–58, 1989; Bronstein I. and McGrath P., Nature 338, 599–600, 1989; Thorpe G. H. and Kricka L. J., Journal of Bioluminescence and Chemiluminescence 3, 97–100, 1989).

However, a disadvantage of luminescent labels is their low signal strength. This is due to the fact that a signal multiplication is not possible in the luminescence measurement i.e. each direct label or each luminescent enzyme substrate molecule is consumed in a single light-generating reaction. Therefore for a long time attempts have been made to eliminate this disadvantage.

Thus for example it is known that the chemiluminescence from the peroxidase (POD)-catalyzed luminol oxidation can be amplified by benzothiazoles (Whitehead T. P. et al., Nature 305, 158–159, 1983), p-substituted phenols such as e.g. p-iodophenols (Thorpe G. H. et al., Clinical Chemistry 31, 1335–1341, 1985; Coyle P. M. et al., Annals of Clinical Biochemistry 23, 42–46, 1986), fluorescein (EP 0 228 046 B1), o- or p-thiazolyl phenols or o- or p-thienyl phenols (EP 0 455 471 A2), hydroxyfluorenones (WO 90/13665). These amplification molecules improve the co-ordination of the light-generating luminol oxidation.

In addition it is known that the alkaline phosphatase-catalyzed chemiluminescence of stabilized triggerable dioxetans can be amplified by polyvinylbenzyl (benzyldimethylammonium)chloride (U.S. Pat. No. 5,145,772 by Bronstein I. et al.; Tropix News Letter on Chemiluminescent Substrates, 1993), polyvinylbenzyl-trialkyl-phosphonium salts (EP 0 561 033 A1 by Schaap A. P.). These hydrophobic polymeric additives displace water from the immediate environment of the products which are formed in an excited state, stabilize these in a hydrophobic medium and thus increase the photon yield.

Amplification of the chemiluminescence of acridinium compounds can be achieved by encapsulation of additionally hydrophobized acridinium ester molecules in liposomes composed of dipalmitoyl phospholipids and cholesterol in order to achieve an accumulation (Law S-J. et al., Journal of Bioluminescence and Chemiluminescence 4, 88–98) or by addition of quaternary phosphonium salts (EP 0 534 380 A1) or micelles of cetyltrimethylammonium bromide to achieve a signal amplification (McCapra F., Accounts of Chemical Research 9, 201–208, 1976). With regard to the mechanism of action, a preference for the light reaction over the dark reaction has been discussed in this case i.e. an increase in the yield of chemical product in the excited state and thus capable of luminescence.

A disadvantage of the above-mentioned amplification measures is that each of these is specific for one particular luminescence system. Therefore the object of the present invention was to provide a method that can be used independently of the respective luminescence system used and if desired in combination with other amplification methods, which leads to an improvement of signal detection in luminescent reactions.

This object is achieved according to the invention by a method for the detection of an analyte in a sample liquid by measurement of luminescence according to the principle of a ligand-receptor assay wherein a sample liquid is incubated with at least one receptor which carries a luminescent label and the presence or/and the amount of the analyte to be detected in the sample liquid is determined by measurement of luminescence which is characterized in that the luminescence is measured in a measuring medium containing dispersed components which cause a randomization of the light produced in the luminescent reaction and if desired results in the formation of a preferred direction in the light scattering.

This randomization or reflection of the light generated in the luminescent reaction caused by the presence of dispersed components surprisingly leads to a considerable increase in the sensitivity and the precision of the luminescence measurement. In addition it is possible by for example immobilizing the luminescent-labelled receptor on a solid phase to achieve a preferred direction for the light scattering due to the layer thickness relationships above and below the light source. These effects are independent of the respective luminescence system used and can therefore be used for a wide range of applications. A further advantage of the method according to the invention is that it can be carried out simply and cost-effectively.

The measurement medium in which the luminescence measurement is carried out in the process according to the invention usually comprises a liquid phase with gaseous, liquid or/and solid components dispersed therein. The dispersion preferably has an adequate stability so that no significant segregation of the dispersed components occurs during the measurement process e.g. by phase separation or sedimentation. When the method according to the invention is carried out in an automatic measuring instrument it is preferable that the dispersion is stable for at least one day, particularly preferably for at least one week and most preferably for at least 3 weeks. Examples of such dispersions are given in the following.

In a preferred embodiment the measuring medium comprises a suspension or a colloidal solution (sol) of solid particles which preferably have a mean diameter of 10 nm to 3 $\mu$m. The solid particles particularly preferably have a mean diameter of 100 nm to 800 nm. Most preferably the solid particles have a mean diameter of 150 nm to 600 nm. The amount of solid particles during the measurement is preferably 0.01–2.5% (mass/vol.) relative to the measuring medium and particularly preferably 0.05–1.5% (mass/vol.).

For reasons of dispersion stability it is preferred that the specific weight of the solid dispersed particles does not differ significantly from the specific weight of the measuring medium and preferably by no more than 25% and particularly preferably by no more than 10%. Examples of this are for instance dispersions of organic polymer particles, e.g. acrylic polymers, styrene polymers e.g. sulfate latices, amidine latices, zwitterion latices which may be functionalized. Further examples are ethylene, propylene, butadiene, vinyl and urethane polymers and copolymers of the above-mentioned polymers. Specific examples are shown in the following Table:

| Polymer | specific density (g/cm$^3$) |
|---|---|
| polymethyl methacrylate | 1.19 |
| polystyrene | 1.05 |
| polyvinyltoluene | 1.027 |
| styrene/butadiene 95/5 (% w) | 1.05 |
| styrene/butadiene 60/40 (% w) | 0.99 |
| vinyltoluene/t.-butylstyrene 63/37 (% w) | 1.00 |

When selecting the dispersed particles one should also take care that reactive groups that may be present on the particles are compatible with the respective luminescence system used.

In another preferred embodiment of the present invention the measuring medium comprises an emulsion or colloidal solution of liquid particles with a mean diameter of preferably 10 nm to 3 µm, particularly preferably of 100 nm to 1500 nm. These liquid particles are present during the measurement preferably in an amount of 0.01–3.5% (mass/vol.) relative to the measuring medium particularly preferably in an amount of 0.1–1.5% (mass/vol.). Examples of stable dispersions containing liquid particles are lipid emulsions in water e.g. homogenized milk or an emulsion of soybean lipids or micellizing substances.

Basically all known luminescent labels are suitable for the method according to the invention e.g. bioluminescent or chemiluminescent direct labels, indirect enzyme-amplified labels or electrochemiluminescent labels. An example of preferred luminescent labels are photoproteins that can be activated by calcium such as aequorin, obelin, clytin, mitrocomin, berovin and mnemiopsin. Aequorin is a bioluminescent protein that can be activated by calcium from the organism Aequorea victoria. The recombinant production of aequorin is described by Stults et al. (Biochemistry 31 (1992), 1433–1442). The isolation and purification of the photoprotein obelin from the organism Obelia longissima is described by Vysotskii et al. (in Biokhimiya 54 (1989), 965–973). The cloning, expression and sequence of obelin is described by Illarionov et al. (J. Bioluminescence and Chemiluminescence 8 (1993), VII. International Symposium-Abstracts, 88). The cloning, expression and sequence analysis of the photoproteins clytin and mitrocomin are described by Inouye and Tsuji (FEBS 315 (1993), 343–346) and Fagan et al. (FEBS 333 (1993), 301–305). Further members of the aequorin family are the photoproteins berovin and mnemiopsin (Ward and Seliger, Biochemistry 13 (1974), 1491–1499 and 1500–1510).

Binding of calcium to the above-mentioned photoproteins leads to a change in conformation by which means the protein is converted into an enzyme which catalyzes an oxidation with emission of light.

Further luminescent labels that are suitable for the present invention are isoluminol or acridinium compounds e.g. aryl esters, N-functionalized salts, benzacridinium compounds or carboxamides. In the case of isoluminol the luminescent reaction is triggered by $H_2O_2/OH^-$ and a catalyst such as microperoxidase or a modified prosthetic group of this catalyst (e.g. deuteroferrihaem). Acridinium compounds are triggered by the sequential addition of $H_2O_2/H_+$ and $OH^-$. The procedure for luminescence immunoassays using isoluminol and acridinium compounds is described for example in Analytical Applications of Bioluminescence and Chemiluminescence (1984), Academic Press, Inc., in particular pp 149–158 and 159–162. Reference is herewith made to this disclosure.

Electrochemiluminescent labels such as luminescent metal chelates are also suitable for the method according to the invention. Luminescent metal chelates are metal chelates which produce a detectable electrochemiluminescent reaction. The metal of these metal chelates is preferably a transitional metal or a rare earth metal. The metal is preferably ruthenium, osmium, rhenium, iridium, rhodium, platinum, indium, palladium, molybdenum, technetium, copper, chromium or tungsten. Ruthenium is most preferred.

The ligands which together with the metal form the metal chelate are usually aromatic polyheterocycles containing nitrogen such as bipyridines, bipyrazoles, terpyridines and phenanthrolines which may be substituted. Bipyridines and phenanthrolines are particularly preferred. Specific examples of suitable metal chelates and the procedure for electrochemiluminescence assays are described in EP-A-0 178 450, EP-A-0 580 979, WO 90/05301, WO 90/11511 and WO 92/14138.

In the method according to the invention the dispersed components can be added to the measuring medium together with the luminescent trigger i.e. with the substance which triggers the luminescent reaction. On the other hand the dispersed components can also be added separately before the trigger.

In the method according to the invention a receptor suitable for detecting the respective analyte is used which carries a luminescent label. This luminescent label may be a group that is directly capable of luminescence or an enzyme which catalyzes a luminescent reaction e.g. peroxidase or alkaline phosphatase. The luminescent label is preferably a group capable of direct luminescence.

The receptor which carries the luminescent label can, depending on the test format, for example be an antibody or antibody fragment, an antigen or a part thereof (e.g. an epitope) or a hapten which if necessary is coupled to a carrier material or a partner of a specific binding pair (e.g. biotin/streptavidin) or a nucleic acid. Processes for coupling luminescent labels to receptors are known from the state of the art and do not need to be discussed in detail.

The method according to the invention is carried out according to the principle of a ligand receptor assay i.e. an analyte present in the sample liquid is detected qualitatively or/and quantitatively by binding to a labelled receptor. Detection of the analyte can for example be achieved in an immunoassay which is based on the specific binding of an antigen to an antibody. On the other hand the analyte can also be detected in a hybridization assay in which a nucleic acid present in the sample liquid is detected by hybridization with a labelled receptor nucleic acid probe. A combination of an immunoassay with a hybridization assay is also possible e.g. by coupling the nucleic acid receptor to a hapten which is recognized by a luminescent labelled antibody.

The method according to the invention can be carried out according to any test format for ligand receptor assays e.g. as a homogeneous immunoassay with only one reaction phase or as a heterogeneous assay with several reaction phases but it is preferred that the method according to the invention should be carried out as a heterogeneous hybridization assay or immunoassay or a combination thereof. In such a heterogeneous assay the luminescent-labelled receptor is incubated with a sample liquid in the presence of at least one reactive solid phase. The luminescent label can be measured in the liquid phase or/and on the solid phase optionally after phase separation. The luminescent label is preferably measured on the solid phase.

In carrying out the method according to the invention it is preferred, especially when the luminescent label is measured on a solid phase, that the luminescence is measured by detection modules which are mounted at the side of or/and below the measuring vessel in which the light generating reaction occurs. The greatest advantages of the inventive addition of dispersed components are achieved in such a method design since the luminescent label on the solid phase, e.g. on the wall of the measuring vessel, is always located at a relatively constant distance from the supporting wall which is typically 3–250 nm.

This distance is too small for the formation of a light-tight layer; this would require a layer thickness of the order of >1 $\mu$m. If the luminescence is measured according to the invention in the presence of dispersed components which for example are added at the end of the immunological reaction together with the trigger, a white reflecting cover is formed above the light source when an adequately large volume is added which, due to the thin layer between the vessel wall and the light source, provides a preferred direction for the light scattering namely laterally or/and towards the bottom.

By this means more light is directed onto a detection module located laterally or/and below the measuring vessel e.g. onto the photosensitive cathode of a photomultiplier tube so that the yield is increased in the signal detection. The gain in sensitivity and precision due to the randomization of the light generated in the luminescent reaction is found in the case of direct labels as well as in the case of enzyme-amplified labels particularly in the case of excited products with a short relaxation time and thus with a low diffusion-dependent distance scatter.

It is preferable to use micromeasuring vessels when carrying out the method according to the invention which enable determination in a volume of 5–1000 $\mu$l and preferably of 10–200 $\mu$l measuring medium.

The present invention in addition concerns the use of a dispersion containing gaseous, liquid or/and solid components dispersed in a liquid in a luminescent ligand receptor assay in order to randomize the light generated in the luminescent reaction and if desired to form a preferential direction in the light scattering. The dispersion is preferably stable within a period of at least one day, particularly preferably of at least one week and in particular of at least 3 weeks. Such a stable dispersion can be advantageously used in an automated detection test procedure.

In addition the dispersion can also contain components necessary to trigger or activate the luminescent reaction. If a photoprotein that can be activated by calcium is used as the luminescent label, the dispersion preferably contains 20 to 200 mmol/l $Ca^{2+}$ ions.

In addition the dispersion can optionally contain buffer substances, preservatives or/and stabilizers.

The present invention in addition concerns a reagent for the detection of an analyte in a sample liquid according to the principle of a ligand receptor assay characterized in that it contains a dispersion of gaseous, liquid or/and solid components in a liquid which effect a randomization of the light generated in the luminescent reaction and if desired the formation of a preferential direction in the light scattering. The reagent is preferably stable within a period of at least one day. In addition the reagent can also contain components necessary to trigger the luminescent reaction.

Finally the invention also concerns a reagent kit for the detection of an analyte in a sample liquid according to the principle of a ligand receptor assay comprising a reagent according to the invention and a receptor spatially separated therefrom which carries a luminescent label.

In addition it is intended to further elucidate the invention by the following examples.

EXAMPLES

In a first set of experiments (examples 1–5) serial dilutions of recombinant aequorin (AquaLite™, SeaLite Sciences Inc. Co.) were prepared and measured with a luminometer. This luminometer was specially designed for a highly sensitive detection of rapid flash kinetics. The detection was from below.

For this 5 $\mu$l of a buffered aequorin solution was placed in each case in miniaturized reaction vessels and the bioluminescent reaction was triggered by injection of 40 $\mu$l $Ca^{2+}$ trigger. The measurement period was alternatively either 1 or 2 seconds. Normal buffered solutions (100 mmol/l $CaCl_2$ in 10 mmol/l Tris-HCl, pH 7.5) or special white dispersions that were stabilized if desired were used comparatively as a calcium trigger.

Additionally both trigger variants were comparatively evaluated in examples 6 to 8 for quantifying TSH and digoxigenin calibration series by means of appropriate one-step bioluminescent immunoassays in which the reaction volume used as well as the incubation period were considerably reduced compared to the present state of the art, but nevertheless it was intended to achieve a high test sensitivity which sets the highest demands on detection sensitivity.

The gain in detected signal as well as the increase in precision and finally the effect on the achievable test sensitivity were examined.

Abbreviations:

| | | |
|---|---|---|
| S/A latex | = | sulfate or amidine latex |
| RLU | = | relative light units |
| RLU/sec | = | relative light units per second |
| cps | = | impulses per second |
| SD | = | standard deviation = standard deviation (with n-1 weighting) |
| CV | 32 | coefficient of variation = $\dfrac{SD}{X} \times 100$ |
| X | = | mean of several measurements |
| intralipid | = | emulsion of soybean oil, phosphatidylcholine and glycerol in water (registered trademark of the Pfrimmer Kabi GmbH & Co. KG company). |

Example 1a

Aequorin label sensitivity of trigger media which contain a lipid emulsion.

Trigger media:

a. 100 mmol/l $CaCl_2$ in 10 mmol/l Tris, pH 7.5
b. homogenized milk, 3.5% fat, diluted 1:20 in Tris/$CaCl_2$

| | Results: stated in [RLU/sec] | |
|---|---|---|
| Aequorin mol/5 µl | trigger a | trigger b |
| 9 × 10⁻¹⁶ | 119,550 | 165,665 |
| 9 × 10⁻¹⁷ | 12,640 | 15,520 |
| 9 × 10⁻¹⁸ | 1,300 | 2,120 |
| 9 × 10⁻¹⁹ | 130 | 185 |
| 9 × 10⁻²⁰ | 22 | 37 |
| blank value | 12 | — |
| F = | 1.00 | 1.42 |

F is the mean quotient of effectivity in the range $10^{-16}$ to $10^{-19}$ mol. The quotient of effectivity of the standard trigger a was used as a reference. It was found that the trigger media which contain a lipid emulsion had better mean quotients of effectivity than the standard trigger.

Example 1b

Aequorin label sensitivity of trigger media which contain a lipid emulsion.

Comparison: clear $CaCl_2$ solution versus white intralipid emulsion (0.48%) in Tris/$CaCl_2$

| Results in [RLU/sec], 0.2–1.2 sec after the start mean valve from quadruplicate measurements | | |
|---|---|---|
| Aequorin [mol/5 µl] | clear trigger (solution) | white trigger (emulsion) |
| 1 × 10⁻¹⁴ | 1,430,116 | 2,081,756 |
| 1 × 10⁻¹⁵ | 152,863 | 283,489 |
| 1 × 10⁻¹⁶ | 15,659 | 26,887 |
| 1 × 10⁻¹⁷ | 1,517 | 2,678 |
| 1 × 10⁻¹⁸ | 217 | 268 |
| 1 × 10⁻¹⁹ | 49 | 105 |
| 1 × 10⁻²⁰ | 4 | 23 |
| buffer blank value | 2 | 6 |
| F | 1.00 | 1.70 |

F = mean quotient of effectivity in the range $10^{-14}$–$10^{-19}$ mol

Example 2

Aequorin label sensitivity of trigger media that contain a latex suspension.

Trigger media:

a. 100 mmol/l $CaCl_2$ in 10 mmol/l Tris, pH 7.5
b. 100 mmol/l $CaCl_2$ in 0.5% suspension of amidine latex (299 nm particle diameter)
c. 100 mmol/l $CaCl_2$ in 0.5% suspension of zwitterion latex (238 nm particle diameter)

Both latices were suspended in 1 mmol/l glycine buffer, pH 7.4 containing 0.1% Tween-20.

| Results: stated in [RLU/2 sec], mean value from quadruplicate measurements | | | |
|---|---|---|---|
| Aequorin mol/5 µl | trigger a | trigger b | trigger c |
| 10⁻¹⁵ | 216,750 | 273,618 | 246,865 |
| 10⁻¹⁶ | 22,670 | 29,169 | 27,108 |
| 10⁻¹⁷ | 1,935 | 2,766 | 2,537 |
| 10⁻¹⁸ | 186 | 317 | 274 |
| 10⁻¹⁹ | 30 | 47 | 32 |
| 10⁻²⁰ | 23 | 23 | 8 |
| blank value | 17 | 15 | 23 |
| r = | 1.00 | 1.00 | 1.00 |
| F = | 1.00 | 1.45 | 1.24 | r = regression analysis in the measurement range $10^{-15}$ to $10^{-19}$ mol. The reference is the standard trigger solution a.
F = mean quotient of effectivity in the range $10^{-15}$ to $10^{-19}$ mol.

Example 3

Influence of the solids content on the aequorin label sensitivity

Trigger media:

a. 100 mmol/l $CaCl_2$ in 10 mmol/l Tris, pH 7.5
b. 100 mmol/l $CaCl_2$ in a 0.5% suspension of amidine latex (299 nm particle diameter)
c. 100 mmol/l $CaCl_2$ in a 1.0% suspension of amidine latex (299 nm particle diameter)

Both latices were suspended in 1 mmol/l glycine buffer, pH 7.4 containing 0.1% Tween-20.

| Results: stated in [RLU / 2 sec] mean value from quadruplicate measurements | | | |
|---|---|---|---|
| Aequorin mol/5 µl | trigger a | trigger b | trigger c |
| 10⁻¹⁵ | 230,061 | 317,802 | 297,537 |
| 10⁻¹⁶ | 23,186 | 33,989 | 31,570 |
| 10⁻¹⁷ | 2,013 | 2,889 | 2,856 |
| 10⁻¹⁸ | 205 | 306 | 324 |
| 10⁻¹⁹ | 30 | 45 | 44 |
| 10⁻²⁰ | 8 | 37 | 13 |
| blank value | 25 | 16 | 23 |
| r = | 1.00 | 1.00 | 1.00 |
| F = | 1.00 | 1.46 | 1.42 | r = regression analysis in the measurement range of $10^{-15}$ to $10^{-19}$ mol. The reference is the standard trigger solution a.
F = mean quotient of effectivity in the range $10^{-15}$ to $10^{-19}$ mol.

Example 4

Influence of particle size ($\leq 299$ nm) on the aequorin label sensitivity

Trigger media:

a. 100 mmol/l $CaCl_2$ in 10 mmol/l Tris, pH 7.5
b. 100 mmol/l $CaCl_2$ in a 0.1% suspension of amidine latex (116 nm particle diameter)
c. 100 mmol/l $CaCl_2$ in a 0.1% suspension of amidine latex (299 nm particle diameter)
d. 100 mmol/l $CaCl_2$ in a 0.1% suspension of zwitterion latex (238 nm particle diameter)

All latices were suspended in 1 mmol/l glycine buffer, pH 7.4 containing 0.1% Tween20.

| Results: stated in [RLU / 2 sec] | | | | |
|---|---|---|---|---|
| Aequorin mol/5 µl | trigger a | trigger b | trigger c | trigger d |
| $10^{-15}$ | 246,869 | 241,232 | 271,882 | 254,887 |
| $10^{-16}$ | 23,823 | 26,386 | 28,875 | 26,712 |
| $10^{-17}$ | 2,272 | 2,346 | 2,713 | 2,677 |
| $10^{-18}$ | 224 | 236 | 240 | 271 |
| $10^{-19}$ | 25 | 29 | 32 | 52 |
| $10^{-20}$ | 8 | 21 | 10 | 12 |
| blank value | 5 | 16 | 16 | 15 |
| r = | 1.00 | 1.00 | 1.00 | 1.00 |
| F = | 1.00 | 1.07 | 1.17 | 1.32 | r = regression analysis in the measurement range $10^{-15}$ to $10^{-19}$ mol. The reference is the standard trigger solution a.
F = mean quotient of effectivity in the range $10^{-15}$ to $10^{-19}$ mol.

Example 5a
Influence of particle size ($\geq 299$ nm) on the aequorin label sensitivity
Trigger media:
 a. 100 mmol/l $CaCl_2$ in 10 mmol/l Tris, pH 7.5
 b. 100 mmol/l $CaCl_2$ in a 0.5% suspension of amidine latex (299 nm particle diameter)
 c. 100 mmol/l $CaCl_2$ in a 0.5% suspension of amidine latex (480 nm particle diameter)
 d. 100 mmol/l $CaCl_2$ in a 0.5% suspension of amidine latex (600 nm particle diameter)

All latices were suspended in 1 mmol/l glycine buffer, pH 7.4 containing 0.1% Tween20. Freshly prepared suspensions were used.

| Results: stated in [RLU / 2 sec] | | | | |
|---|---|---|---|---|
| Aequorin mol/5 µl | trigger a | trigger b | trigger c | trigger d |
| $10^{-15}$ | 210,459 | 267,907 | 267,945 | 303,296 |
| $10^{-16}$ | 20,162 | 25,932 | 30,194 | 32,227 |
| $10^{-17}$ | 1,729 | 2,492 | 3,137 | 3,138 |
| $10^{-18}$ | 167 | 253 | 280 | 320 |
| $10^{-19}$ | 17 | 57 | 48 | 38 |
| $10^{-20}$ | 8 | 28 | 25 | 14 |
| blank value | 10 | 11 | 22 | 20 |
| r = | 1.00 | 0.9999 | 0.9998 | 0.9999 |
| F = | 1.00 | 1.77 | 1.82 | 1.80 | r = regression analysis in the measurement range of $10^{-15}$ to $10^{-19}$ mol. The reference is the standard trigger solution a.
F = mean quotient of effectivity in the range $10^{-15}$ to $10^{-19}$ mol.

Example 5b
Influence of particle size ($\geq 299$ nm) on the aequorin label sensitivity
Trigger media:
 a. 100 mmol/l $CaCl_2$ in 10 mmol/l Tris, pH 7.5
 b. 100 mmol/l $CaCl_2$ in a 0.5% suspension of amidine latex (299 nm particle diameter)
 c. 100 mmol/l $CaCl_2$ in a 0.5% suspension of amidine latex (480 nm particle diameter)
 d. 100 mmol/l $CaCl_2$ in a 0.5% suspension of amidine latex (600 nm particle diameter)

All latices were suspended in 1 mmol/l glycine buffer, pH 7.4 containing 0.1% Tween20. The suspensions were stored for 3 weeks at 4° C.

| Results: stated in [RLU / 2 sec] | | | | |
|---|---|---|---|---|
| Aequorin mol/5 µl | trigger a | trigger b | trigger c | trigger d |
| $10^{-15}$ | 198,120 | 286,136 | 290,122 | 275,504 |
| $10^{-16}$ | 17,951 | 32,957 | 25,881 | 27,818 |
| $10^{-17}$ | 1,761 | 2,895 | 2,614 | 2,535 |
| $10^{-18}$ | 188 | 275 | 302 | 281 |
| $10^{-19}$ | 16 | 36 | 43 | 32 |
| $10^{-20}$ | 8 | 17 | 23 | 23 |
| blank value | 13 | 21 | 21 | 11 |
| r = | 1.00 | 0.9997 | 0.9999 | 0.9999 |
| F = | 1.00 | 1.73 | 1.74 | 1.57 | r = regression analysis in the measurement range $10^{-15}$ to $10^{-19}$ mol. The reference is the standard trigger solution a.
F = mean quotient of effectivity in the range $10^{-15}$ to $10^{-19}$ mol.

Example 6
Use of a white trigger preparation in a TSH bioluminescent immunoassay A mixture of 13 µl standard solution and 27 µl test buffer were placed in miniaturized reaction vessels coated with streptavidin. The test buffer contained $2 \times 10^{-8}$ mol/l biotinylated anti-TSH-IgG and ca. $10^6$ RLU/sec of an anti-TSH-IgG-aequorin conjugate which had been prepared by coupling maleimide-activated anti-TSH antibodies to SH group of aequorin that had been introduced by prior reaction with 2-iminothiolane. Each of the biotinylated and luminescent-labelled antibodies was directed towards different epitopes of TSH. After a 15-minute simultaneous incubation at room temperature without shaking, solid phase-bound conjugate immobilized via immunocomplexes was separated from unbound conjugate still present in the liquid phase. Afterwards the aequorin bioluminescence was triggered in a luminometer by addition of 100 mmol/l $Ca^{2+}$ ions in each case:

A. firstly with $Ca^{2+}$ ions dissolved in 10 mmol/l Tris-buffer, pH 7.5 (normal trigger)
B. secondly with $Ca^{2+}$ ions dissolved in 1 mmol/l glycine buffer in which colourless amidine latex beads (480 nm particle size) were suspended at a concentration of 0.5% solids content (=white trigger)

| Result: The following calibration curves were obtained: | | | |
|---|---|---|---|
| Calibrator [µU TSH/ml] | A $Ca^{2+}$/normal trigger [RLU/s bound] | B $Ca^{2+}$/white trigger [RLU/s bound] | B/A |
| 0.0 µU/ml | 29 ± 8 | 36 ± 3 | 1.24 |
| 0.50 µU/ml | 177 | 289 | 1.63 |
| 4.64 µU/ml | 1483 | 2553 | 1.92 |
| 9.05 µU/ml | 3003 | 5767 | 1.02 |
| 21.81 µU/ml | 6754 | 13486 | 2.00 |
| 42.78 µU/ml | 14195 | 27075 | 1.91 |
| Dynamic [a] | 489 | 759 | |
| Sensitivity [b] | 0.054 µU TSH/ml | 0.012 µU TSH/ml | |

[a] = Quotient highest / lowest standard
[b] = calculated from the mean of quadruplicate measurements of the zero standard plus twice the standard deviation based on the signal and converted by linear regression into concentrations.

This experiment demonstrates the potential of the method according to the invention for an increased analytical sensitivity in bioluminescent immunoassays.

Example 7

Use of a white trigger preparation in a DIG bioluminescent immunoassay

A mixture of 13 µl standard solution of a heptapeptide having the sequence Ser-Gln-Asn-Tyr-Pro-Ile-Val which had been biotinylated and labelled with digoxigenin and 27 µl test buffer that contained ca. $2\times10^6$ RLU/s anti-DIG-Fab aequorin conjugate were pipetted into miniaturized reaction vessels coated with streptavidin.

After a 15-minute simultaneous incubation at room temperature without shaking, solid phase-bound conjugate immobilized via immunocomplexes was separated from unbound conjugate still present in the liquid phase.

Afterwards the aequorin bioluminescence was triggered in a luminometer by addition of look mmol/l $Ca^{2+}$ ions in each case:
1: firstly with $Ca^{2+}$ ions dissolved in 10 mmol/l Tris-buffer, pH 7.5 (normal trigger)
B. Secondly with $Ca^{2+}$ ions dissolved in 1 mmol/l glycine buffer in which colourless amidine latex beads (600 nm particle size) were suspended at a concentration of 0.5% solids content (=white trigger)
Result: The following calibration curves were obtained:

| DIG assay 1 (normal trigger) | | | |
|---|---|---|---|
| | Individual measurements | Mean ± SD | Factor X/A |
| Calibrator A<br>0 pmol/l | 83<br>103<br>112<br>71 | 92 cps ± 19<br>20% CV | |
| Calibrator B<br>0.2 pmol/l | 187<br>133<br>239<br>259 | 205 cps | 2.22 |
| Calibrator C<br>2 pmol/l | 1056<br>895 | 976 cps | 10.57 |
| Calibrator D<br>20 pmol/l | 8826<br>8416 | 8621 cps | 93.45 |
| Calibrator E<br>200 pmol/l | 83419<br>73349 | 78384 cps | 849.69 |
| Calibrator F<br>1000 pmol/l | 305260<br>240287 | 272774 cps | 2956.89 |

Lower detection limit (LDL):
LDL (A + 2 × SD, linear regression) = $8.7 \times 10^{-19}$ mol DIG = $5.3 \times 10^5$ DIG molecules

| DIG-assay 2 (white trigger) | | | |
|---|---|---|---|
| | Individual measurements | Mean ± SD | Factor X/A |
| Calibrator A<br>0 pmol/l | 160<br>180<br>181<br>137 | 165 cps ± 21<br>13% CV | |
| Calibrator B<br>0.2 pmol/l | 347<br>356<br>498<br>258 | 365 cps | 2.22 |
| Calibrator C<br>2 pmol/l | 1508<br>1155 | 1332 cps | 8.09 |
| Calibrator D<br>20 pmol/l | 11099<br>11485 | 11292 cps | 68.64 |
| Calibrator E<br>200 pmol/l | 108984<br>102122 | 105553 cps | 641.66 |
| Calibrator F<br>1000 pmol/l | 392615<br>424763 | 408689 cps | 2484.43 |

Lower detection limit (LDL):
LDL (A + 2 × SD, linear regression) = $3.4 \times 10^{-19}$ mol DIG = $2.0 \times 10^5$ DIG molecules This again shows the potential of the method according to the invention for improving signal detection, precision and thus also analytical sensitivity.

Example 8

Use of a white trigger preparation in a DIG bioluminescent immunoassay

The experimental design was as in example 7. Particular attention was paid to the precision in the lower concentration range. $1.5\times10^6$ RLU/s of a highly purified <DIG>-Fab aequorin 1:1 conjugate were used per test and streptavidin-coated reaction vessels from a production batch that was given a very good functional rating. In this experiment the increase in precision due to signal amplification and randomization was especially apparent.

Result: The following calibration curves were obtained:

| DIG-assay 1 (normal trigger) | | | |
|---|---|---|---|
| | Individual measurements | Mean ± SD | Factor X/A |
| Calibrator A<br>0 pmol/l | 112<br>141<br>86<br>99 | 110 cps ±<br>24<br>21% CV | |
| Calibrator B<br>0.2 pmol/l | 188<br>170<br>145<br>144 | 162 cps ±<br>21<br>13% CV | 1.48 |
| Calibrator C<br>2 pmol/l | 883<br>772 | 828 cps | 7.56 |
| Calibrator D<br>20 pmol/l | 8007<br>7349 | 7678 cps | 70.12 |
| Calibrator E<br>200 pmol/l | 85774<br>74418 | 80096 cps | 731.47 |
| Calibrator F<br>1000 pmol/l | 249480<br>246125 | 247803 cps | 2263.04 |

Lower detection limit (LDL):
LDL (A + 2 × SD, linear regression) = $2.4 \times 10^{-18}$ mol DIG = $1.45 \times 10^6$ DIG molecules

| DIG-assay 2 (white trigger; 0.5% solids content) | | | |
|---|---|---|---|
| | Individual measurements | Mean ± SD | Factor X/A |
| Calibrator A<br>0 pmol/l | 167<br>164<br>150<br>159 | 160 cps ±<br>7<br>5% CV | |
| Calibrator B<br>0.2 pmol/l | 254<br>253<br>294<br>289 | 273 cps ±<br>22<br>8% CV | 1.70 |

-continued

DIG-assay 2 (white trigger; 0.5% solids content)

|  | Individual measurements | Mean ± SD | Factor X/A |
|---|---|---|---|
| Calibrator C 2 pmol/l | 1302 1123 | 1213 cps | 7.55 |
| Calibrator D 20 pmol/l | 11789 11061 | 11425 cps | 71.41 |
| Calibrator E 200 pmol/l | 94536 110458 | 102497 cps | 640.61 |
| Calibrator F 1000 pmol/l | 424678 385461 | 405070 cps | 2531.68 |

Lower detection limit (LDL):
LDL (A + 2 × SD, linear regression) = $3.2 \times 10^{-19}$ mol DIG = $2.0 \times 10^5$ DIG molecules

We claim:

1. A method for the determination of an analyte in a sample liquid, comprising:
   incubating the sample liquid with at least one receptor which carries a chemiluminescent label, a bioluminescent label or an electrochemiluminescent label and which is specific for the analyte to be determined to bind the analyte and the at least one receptor,
   triggering a luminescence reaction to cause light to be emitted from the label, and reflecting at least a portion of the light so emitted in a predetermined direction, using components which are dispersed in a measuring medium, to concentrate the emitted light in a predetermined location, and
   measuring the concentrated light in the predetermined location and correlating the measured light with a presence and/or an amount of the analyte.

2. The method of claim 1, wherein the measuring medium comprises a liquid phase containing liquid and/or solid components dispersed therein.

3. The method of claim 1, wherein the measuring medium contains a suspension or colloidal solution of solid particles having a mean diameter of 10 nm to 3 μm.

4. The method of claim 3, wherein the solid particles have a mean diameter of 100 nm to 800 nm.

5. The method of claim 3, wherein the solid particles are present during the measuring step in a proportion of 0.01–2.5% mass/vol relative to the measuring medium.

6. The method of claim 3, wherein the solid particles comprise organic polymers or copolymers.

7. The method of claim 6, wherein the organic polymers or copolymers are selected from the group consisting of acrylic, styrene, ethylene, propylene, butadiene, vinyl and urethane.

8. The method of claim 1, wherein the measuring medium comprises an emulsion or colloidal solution containing liquid particles having a mean diameter of 10 nm to 3 μm.

9. The method of claim 8, wherein the liquid particles have a mean diameter of 100 nm to 1.5 μm.

10. The method of claim 8, wherein the liquid particles are present during the measuring step in a proportion of 0.01–3.5% mass/vol relative to the measuring medium.

11. The method of claim 8, wherein the liquid particles are lipid particles.

12. The method of claim 1, wherein the label is selected from the group consisting of isoluminol, an acridinium compound and a photoprotein which emits light in the triggering step by reacting with a calcium compound.

13. The method of claim 12, wherein the label is selected from the group consisting of aequorin, obelin, clytin, mitrocomin, berovin and mnemiopsin, and the label emits light in the triggering step by reacting with a calcium compound.

14. The method of claim 1, wherein the label is a luminescent metal chelate.

15. The method of claim 14, wherein the chelate is selected from the group consisting of ruthenium, rhenium, osmium, chromium and iridium.

16. The method of claim 1, wherein in the incubating step, the at least one receptor is incubated with the sample liquid in the presence of at least one solid phase which binds to the analyte and/or the at least one receptor.

17. The method of claim 16, wherein the label is bound to the solid phase before the measuring step.

18. The method of claim 1, wherein the measuring medium is contained in a reaction vessel having at least one side and a bottom and detection modules are located at the at least one side of the reaction vessel and below the bottom of the reaction vessel, in the triggering step, the emitted light is concentrated toward the detection modules, and in the measuring step, the concentrated light is measured by the detection modules.

19. The method of claim 1, wherein the measuring step is conducted with a volume of 5–1000 μl of measuring medium.

20. The method of claim 1, wherein the method is an immunoassay.

21. The method of claim 1, wherein the triggering step is conducted in the measuring medium.

22. The method of claim 21, wherein the measuring medium further comprises components for triggering the luminescence reaction in the triggering step.

23. The method of claim 1, wherein the at least one receptor is immobilized on a solid phase.

24. The method of claim 1, wherein the method is a hybridization assay.

* * * * *